US00PP23376P3

(12) United States Plant Patent
Peterson et al.

(10) Patent No.: US PP23,376 P3
(45) Date of Patent: Feb. 5, 2013

(54) GRAPEVINE PLANT NAMED 'NOKOMIS'

(50) Latin Name: *Vitis* hybrid
Varietal Denomination: Nokomis

(75) Inventors: Kevin Peterson, Chisago City, MN (US); Kyle Peterson, Minneapolis, MN (US)

(73) Assignee: Winehaven, Inc., Chisago City, MN (US)

( * ) Notice: Subject to any disclaimer, the term of this patent is extended or adjusted under 35 U.S.C. 154(b) by 107 days.

(21) Appl. No.: 12/932,614

(22) Filed: Mar. 1, 2011

(65) Prior Publication Data

US 2012/0227147 P1 Sep. 6, 2012

(51) Int. Cl.
*A01H 5/00* (2006.01)

(52) U.S. Cl. ..... Plt./205; Plt./206

(58) Field of Classification Search ..... Plt./205, Plt./206

See application file for complete search history.

*Primary Examiner* — Kent L Bell

(74) *Attorney, Agent, or Firm* — Patterson Thuente Christensen Pedersen, P.A.

(57) ABSTRACT

A grapevine cultivar having a combination of good winter hardiness, vigor, grape cluster size, disease resistance and overall suitability as a red wine grape; the vine is winter hardy to about −40 degrees F. (about −40 degrees C.) and the grape is well-suited to the commercial production of Ice Wine because its grape clusters have a tendency to resist splitting and falling off the cluster after a hard freeze; the grapevine also produces relatively large clusters of grapes that are beneficial to commercial production.

6 Drawing Sheets

Botanical classification: *Vitis* hybrid.
Variety denomination: 'NOKOMIS'.

BACKGROUND OF THE INVENTION

Growing wine grapes in Minnesota on a commercial scale is a relatively new endeavor because the region's mid-continental climate yields exceptionally cold winters that create challenges for the emerging wine industry. At the same time, the cold climate in Minnesota creates opportunities for the production of Ice Wine, which is made from grapes frozen on the vine in the traditional German style. The freezing and thawing of the grapes dehydrates the fruit, concentrates the sugars and acids, and extracts flavors in the berries, thereby intensifying the flavors and adding complexity to the wine made from it. A rare delicacy in the wine world, Ice Wine is becoming increasingly rare as traditional winegrowing regions have experienced warmer temperatures than average during recent years.

At present, less than 30 wineries exist in Minnesota, extending from southern Minnesota to just south of the Canadian border. Many of these wineries produce non-grape wines from honey, rhubarb, raspberries, and the other fruit. However, several Minnesota wineries are currently managing substantial vineyard tracts. A few wineries have even received awards for wines produced by these vineyards at top international wine competitions. However, production of Ice Wine in Minnesota remains difficult because many known grapevine varieties have a tendency for their fruit to split and fall from the cluster after a hard freeze.

Despite some success, grape growing in Minnesota is fraught with difficulties. Most European grape varieties that are grown in Minnesota, and even many "French-American hybrid" wine varieties, require protection if they are to survive the frigid winters—especially in northern Minnesota.

This is usually done by removing vines from the trellises and bending them to the ground in early November, then covering the vine with soil or straw.

Although covering vines effectively insulates them from cold winter temperatures, there are a number of problems that make this practice less than satisfactory. Of primary concern is the greatly increased labor cost, which is generally prohibitive and makes it quite difficult for Minnesota vineyards to operate profitably. However, logistical challenges exist as well. For example, the trunks of the vine may break due to the fact that they become less pliable as they grow larger in diameter. If the vine does not break, fungi and bacteria may infiltrate the vine through small "stress cracks" in the trunk, causing disease. Rodents commonly feed on the trunks and canes as they lay on the ground during the winter, further injuring the vine. If the vine survives the winter, great care must be taken to avoid damaging the buds when the vines are uncovered during the spring. Accordingly, for grapevines to be of high commercial value to vineyards in northern regions, it is nearly essential for varieties to be hardy enough to remain on the trellises throughout the winter months without removal and winter covering.

Fortunately, there exist good sources of tolerance to cold hardiness for breeding purposes, i.e. *Vitis riparia* and *Vitis labrusca*. These hardy grapes have a flavor that is acceptable in table wines. However, they are too high in acid and too unproductive to use on their own.

Some of the hardiest known wine grape varieties, 'Sabrevois' (ES 2-1-9), and 'Frontenac' (MN 1047), have demonstrated hardiness to at least −35 degrees F. (about −37.2 degrees C.) in Chisago City, Minn. A relatively new variety, the 'Chisago' grape (U.S. Plant Pat. No. 19,246) has been shown to be winter hardy to about −40 degrees F. (about −40 degress C.). At this location, the present variety has proven that it is at least as winter hardy as these known varieties. The present variety also presents a wide variety of additional distinguishing characteristics including vigor, productivity, resistance to disease and pests, size of fruit, size of grape clusters, coloration, and flavor, ability to retain cluster integrity and resist cracking after a freeze, hereinafter set forth in detail.

SUMMARY OF THE INVENTION

The present invention relates to a new and distinct cultivar of grapevine plant botanically known as *Vitis* hybrid 'Nokomis', referred to hereinafter by its cultivar name, 'Nokomis'. The 'Nokomis' grapevine has a unique combination of hardiness, vigor, disease resistance, and wine quality not found in existing grape varieties known to the Inventors. It is also well-suited to the commercial production of Ice Wine because its grape clusters have a tendency to resist splitting and falling off the cluster after a hard freeze. Moreover, 'Nokomis' produces relatively large clusters of grapes that are beneficial to commercial production.

Fruit of 'Nokomis' can be fermented to produce red wine having a deep red color and desirable aromas of cherry, blueberry, raspberry, and blackberry. The wine lacks "foxy" aromas typically associated with *V. labrusca*. It also lacks herbaceous aromas that are commonly associated with *V. riparia*. The fruit at harvest is usually slightly lower in sugar and higher in acidity than wines associated with *V. vinifera*.

When grown in east central Minnesota, the plants of 'Nokomis' are extremely vigorous and winter hardy to at least −40 degrees F. (−40 degrees C.). The vines are moderately susceptible to herbicide injury and moderately susceptible to foliar phylloxera (*Daktulospahira vitifoliae*) damage. The disease black rot, caused by *Guignardia bidwellii*, has been observed sporadically and at low levels on the leaves, but not on the fruit. Downy mildew, caused by *Plasmopara viticola*, has been observed at moderate levels on the foliage, but has not been seen on the fruit. Powdery mildew disease, caused by *Uncinula necator*, has been seen at low levels on the foliage, but not on the fruit.

'Nokomis' vines set a relatively heavy crop load from year to year that varies with pruning technique. The fruit are borne on loose, large clusters. The berries are medium sized and blue-black in color with a waxy bloom at maturity. The berries resist prematurely separating from the cluster, and have consistently been observed hanging on the vine well after harvest, and more than a month after a hard freeze, making the present variety well suited for the production of Ice Wine. The berries have not been observed to split, even under wet conditions in the autumn.

BRIEF DESCRIPTION OF THE DRAWINGS

The accompanying color photographs show characteristics of 'Nokomis' grown under typical field conditions in east central Minnesota. The photographs depict the color features as true as is reasonably possible.

DETAILED BOTANICAL DESCRIPTION

Figure 1:
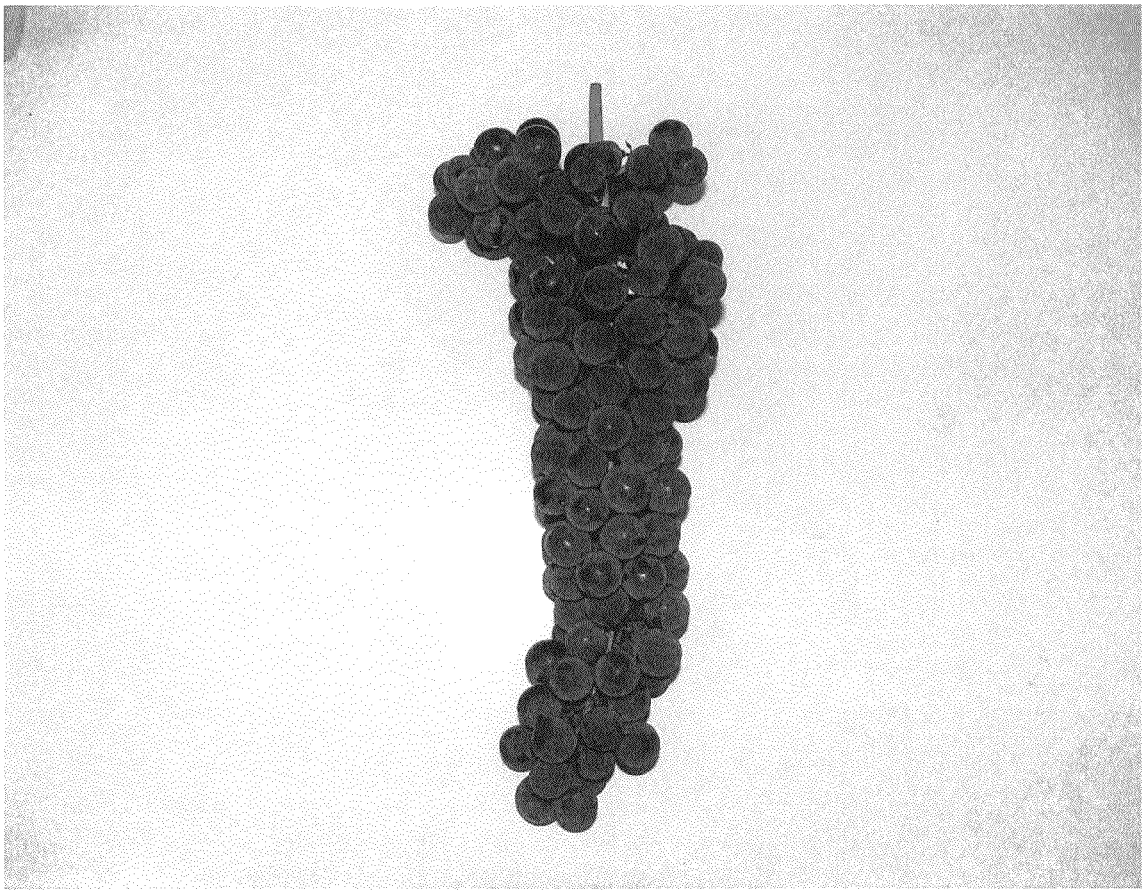
FIG. 1. shows a close-up of a fruit cluster of 'Nokomis' in mid August.
Figure 2:
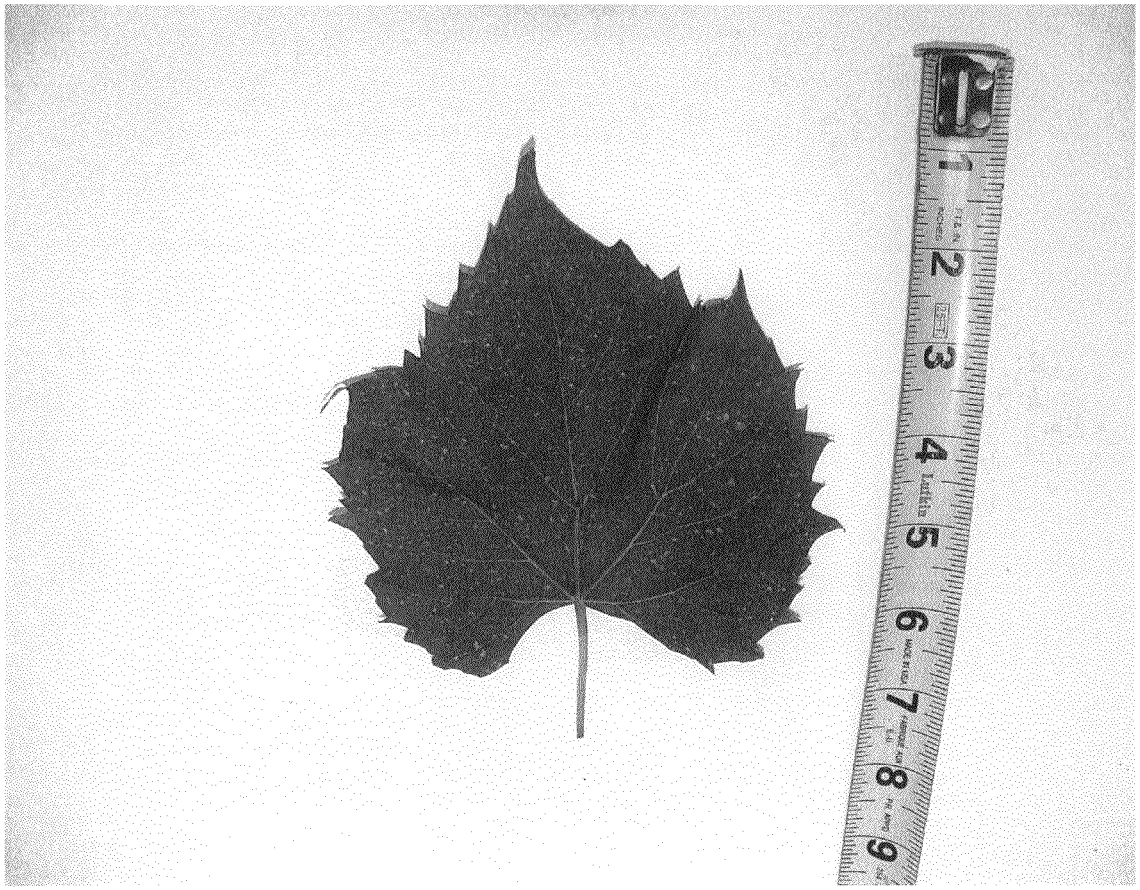
FIG. 2. shows a mature leaf, upper surface in mid August.
Figure 3:
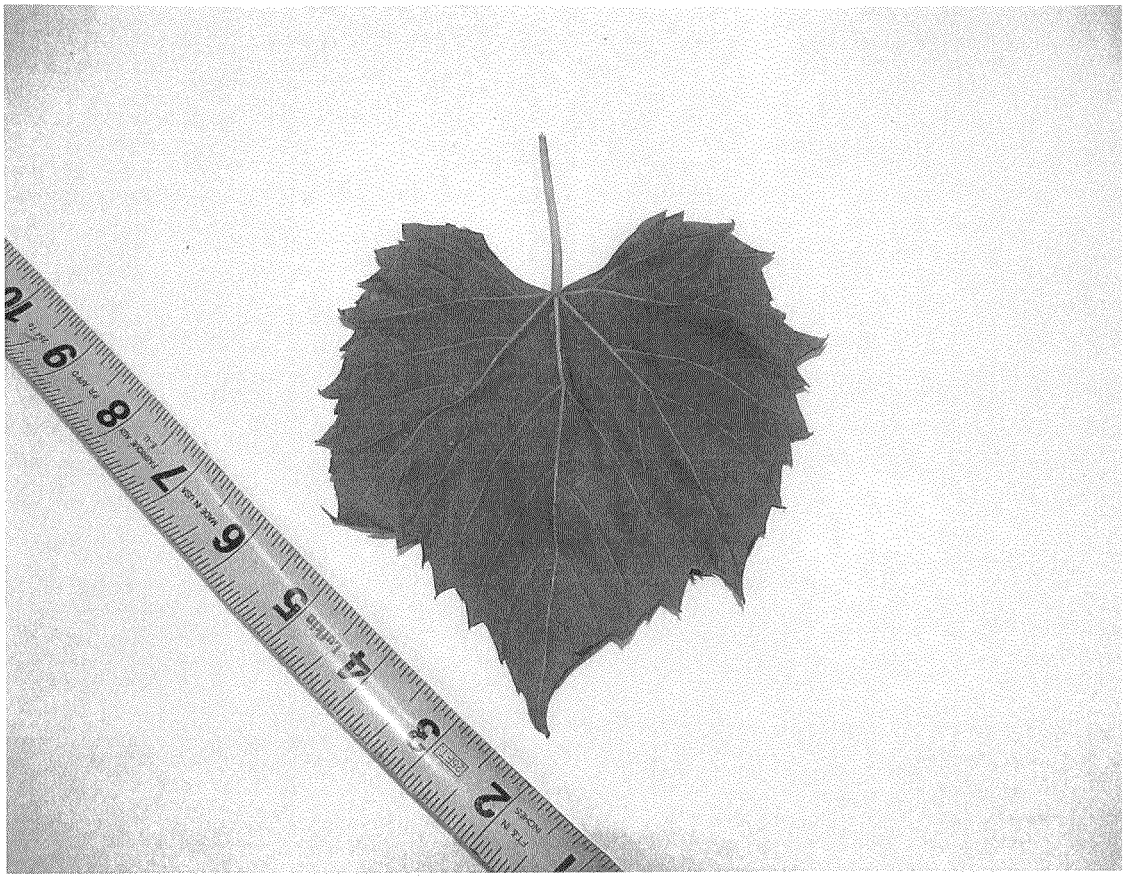
FIG. 3. shows a mature leaf, lower surface in mid August.
Figure 4:
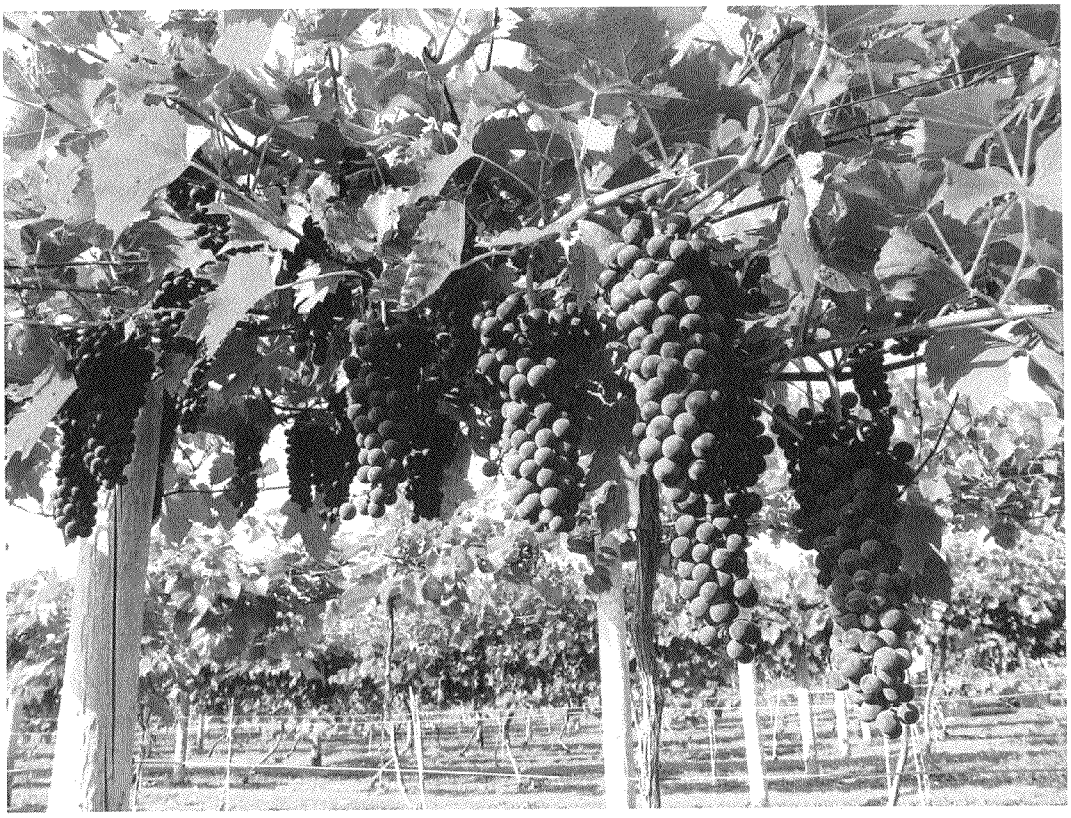
FIG. 4. shows a mature vine in mid August.
Figure 5:
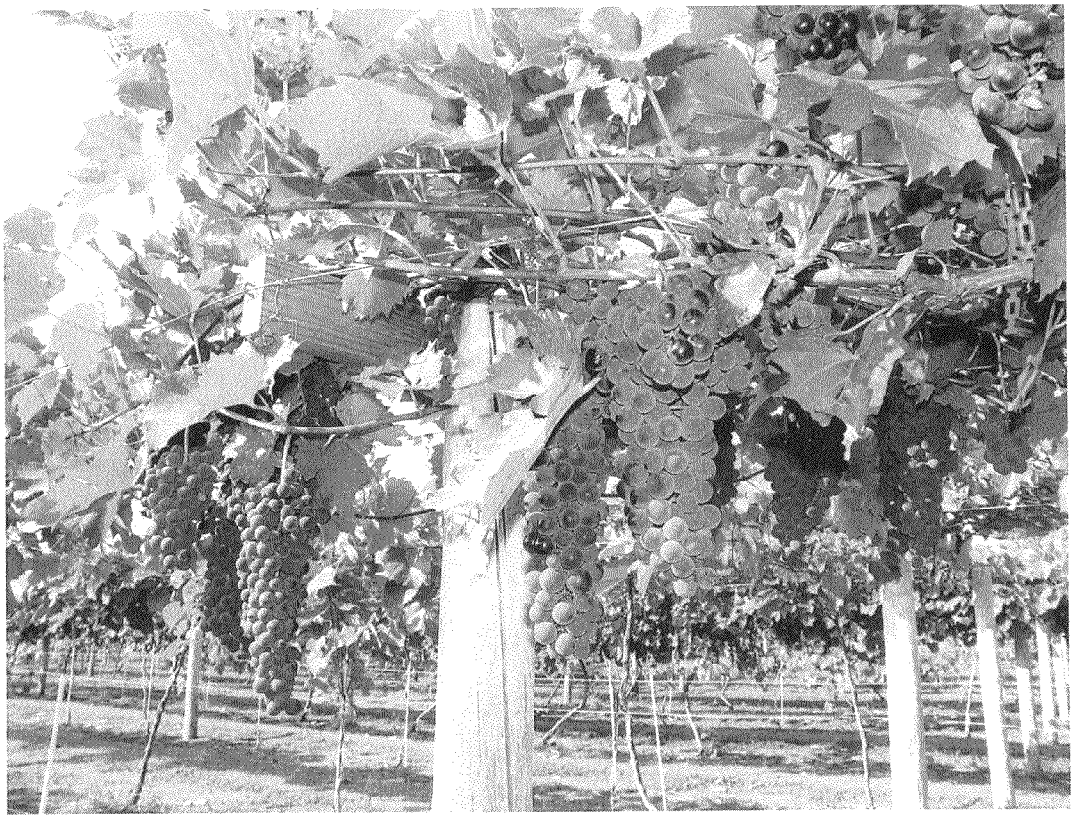
FIG. 5 shows an alternative image of a mature vine in mid August.
Figure 6:
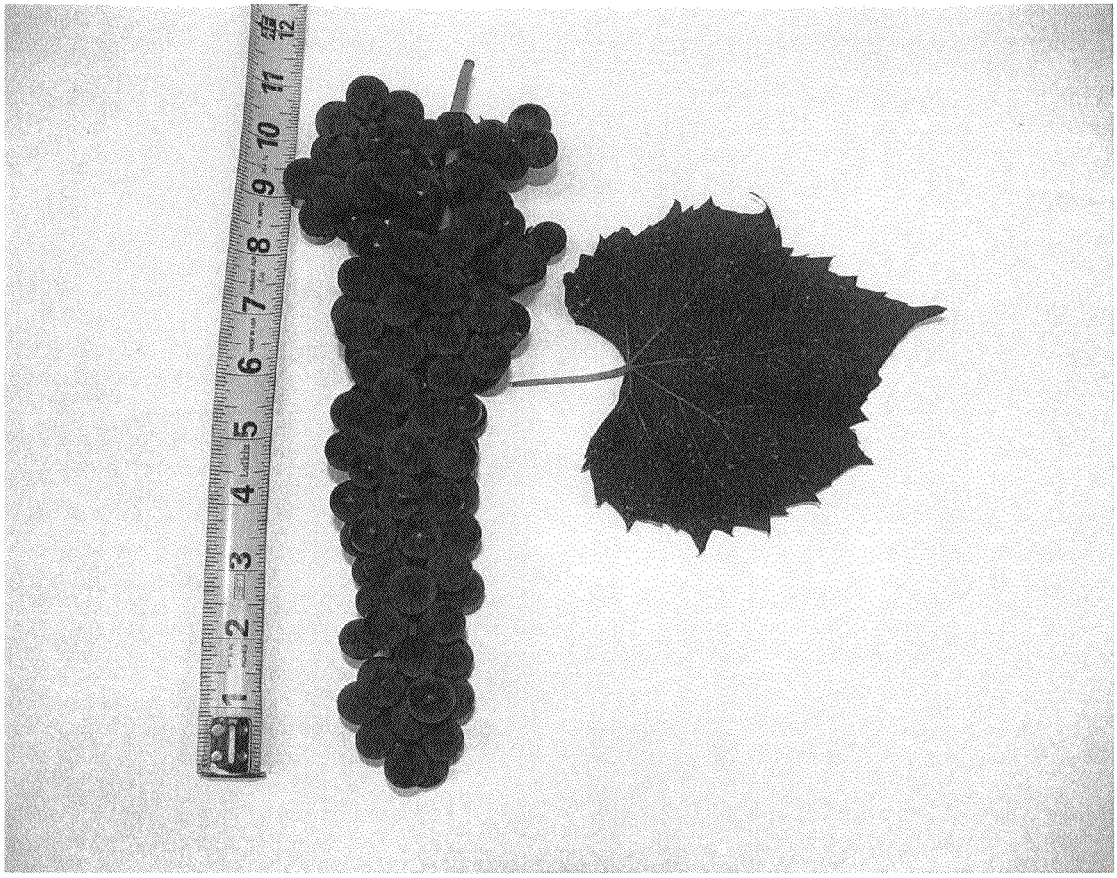
FIG. 6 shows a mature fruit cluster of 'Nokomis' alongside a mature leaf in mid August.

'Nokomis' was selected for its combination of good winter hardiness, vigor, grape cluster size, disease resistance and overall suitability as a red wine grape. It arose as a result of the inventors' grape breeding program to develop commercially viable wine grape varieties to complement non-grape wines produced at their winery.

The grapevine of the present invention was discovered by the inventors among a number of cross combinations in the breeding program. The breeding program produced several test seedlings which were evaluated for their characteristics related to a variety of considerations including, but not limited to, hardiness, vigor, disease resistance, and commercial potential as a wine grape variety. The grapevine was discovered in a controlled cross of the grape 'St. Croix' (U.S. Plant Pat. No. 4,928) ('ES114' times 'Seyval') times ('Minn 78' times 'Seneca'), which was the female parent, and the grape 'Chisago' (U.S. Plant Pat. No. 19,246), which was the male parent. The inventors have identified the present variety as 'KP 16' and selected the name 'Nokomis' therefor.

The inventors have asexually reproduced the present variety in Chisago City, Minn. by means of cuttings, and have carefully observed the variety for approximately 7 years. The following data pertains to vines grown in Chisago City, Minn. Alphanumeric color designations refer to values based on the 1995 R.H.S. Color Chart published by The Royal Horticultural Society, London, England. Many of the descriptors are based on those set forth by the International Board for Plant Genetic Resources in collaboration with the Office Internationale de la Vine et du Vin (OIV) and the International Union for the Protection of New Varieties of Plants.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected. Botanical Classification: Cultivar of *Vitis* with ancestry tracing to several species including *V. labrusca* and *V. riparia*. Parentage: 'St. Croix' (female), 'Chisago' (male).

Plants of 'Nokomis' are stable and reproduced true to type in successive generations. 'Nokomis' has perfect flowers containing extended stamens with anthers having viable pollen. When ripe, the berries of 'Nokomis' are blue-black in color 202A with 98D bluish bloom.

The present invention has been shown to be winter hardy to at least −40 degrees F. (−40 degrees C.) in Chisago City, Minn. By way of comparison, the grapevine 'Nokomis' is slightly more winter hardy than its female parent, 'St. Croix,' which is hardy to about −32 degrees F. (about −35.6.degrees C.). By, contrast, 'Nokomis' is about as winter hardy as its male parent, 'Chisago,' which is hardy to about −40 degrees F. (about −40 degrees C.). The values presented below are means (with ranges in parentheses) from vines observed during the 2010 growing season.

Vine:

*Size and vigor*.—Size. — Vines are large and grow best in rows with 8 feet (about 2.4 meters) of spacing between vines. Vigor. — Vigorous — new vines propagated from cuttings were established in a greenhouse on Mar. 3, 2007 and transplanted to a new vineyard located in Chisago City, Minn. on May 12, 2007. Over 75% of the new vines grew at least 4 feet (about 1.2 meters) by Sep. 1, 2007. The inventors have also found it beneficial to train the vine to grow only a single trunk to reduce crowding due to plant vigor in a given growing season.

*Productive capacity*.—In vineyards located in Chisago City, Minn., 'Nokomis' vines in experimental plots have consistently produced 8.19 Kg/vine or the equivalent of 5.4 tons of ripe fruit per acre.

*Canes*.—Canes are medium length 5' (about 152 cm) to 10' (about 305 cm).

*Color of canes*.—Brown; 175A, 175B, 175C.

*Thickness of canes*.—Medium. Average width at node is 0.5 inch (about 15.2 cm).

*Diameter at base*.—3.1 inches (about 7.9 cm) to 4.7 inches (about 11.9 cm).

*Diameter at midpoint*.—1.9 inch (about 4.8 cm) to 3.5 inch (about 8.9 cm). Typical observed internode cane length 4" (about 10.2 cm) to 12" (about 30.5 cm).

*Cane surface texture*.—Smooth (both mature and immature canes).

*Shoots*.—Length of shoots: medium to long, approximately 6.5 inches (about 16.5 cm). Internode length: approximately 3 inches (about 76 mm). Width at node — approximately 0.5 inches (12.7 mm). Shape — predominately circular. Diameter — approximately 9 mm. Contour — smooth. Color of shoots 144A, 144B, yellow-green.

*Growing tip*.—Generally hang over wires.

*Tendrils*.—Length of tendrils: 4 inches (10.16 mm) to 7 inches (17.78 mm). Texture of tendrils: smooth. Color of tendrils 166A, 166C. Typical and observed tendril diameter: 1 mm to 4 mm. Typical and observed tendril shape: round.

*Buds*.—Shape of buds: pointed. Size of buds: medium, approximately 4 mm times 5 mm. Position of buds — markedly held out at approximately 45 degree angle. Cane bud fruitfulness — basal most fruitful. Bud color: 166B. Bud break: near Chisago City, bud break is during the middle of May.

*Trunk*.—Bark texture — moderately flaky, small vertical segments approximately 0.40 cm times 6.0 cm. Bark color: striated, 201C and 201D.

Leaves: Ten representative mature leaves from different vines were examined during the 2009 and 2010 growing seasons. The leaves were pressed and dried for later analysis. The values presented below are ranges from collections during August of each year.

*Length of mature leaf*.—4 inches (101.6 mm) to 7 inches (177.8 mm).

*Width of mature leaf*.—3.5 inches (88.9 mm) to 6.5 inches (165.1 mm).

*Leaves*.—Shape. — Cordiform (heart shaped); inferior lateral sinuses and superior lateral sinuses deep with an approximate 1:1 length to width ratio. Apex. — Pointed. Base. — Rounded.

*Number of lobes*.—3.

*Anthocyanin coloration of main veins on the upper side of the blade*.—Wery weak — red 59C.

*Mature leaf profile*.—Flat.

*Blistering surface of blade upper surface*.—Absent.

*Leaf blade tip*.—In the plane of the leaf.

*Margins*.—Serrate with irregular teeth.

*Height of teeth on margin* (*average*).—0.31 cm (ranges from 0.2 cm to 0.9 cm; height/width ratio is approximately 0.25 (ranges from 0.10 to 0.43).

*Shape of teeth on margin*.—Wide teeth with convex sides.

*Texture* (*mature leaf*).—Upper surface: Smooth to slightly bullate; glabrous. Lower surface: Smooth; almost glabrous with sparse short hairs on veins.

*General shape of petiole sinus*.—Slightly open.

*Tooth at petiole sinus*.—Absent.

*Petiole sinus limited by veins*.—Absent.

*Shape of upper lateral sinus*.—Lobes slightly overlapping. On mature leaf, petiole sinus is 1.47 inches (3.7 cm) long and 0.52 inches (1.3 cm) wide at widest point.

*Autumn coloration of leaves*.—Near grayed-yellow 162A on upper leaf surface, near yellow-green 153D on lower leaf surface. Coloration is slow to develop. Normally frost kills leaves before extensive color change.

*Texture of upper surface of leaf*.—Smooth.

*Texture of lower surface of leaf*.—Rough.

*Length of petiole*.—4 inches (101.6 mm) to 5 inches (127 mm).

*Shape of petiole*.—Mostly round.

*Diameter of petiole*.—3.1 mm.

*Color of petiole*.—145A.

*Color of adaxial leaf surface*.—146A, 146B, yellow-green leaf surface.

*Color of abaxial leaf surface*.—146C, yellow-green leaf surface. Pubescence very sparse on main veins abaxial surface and at petiolar junction.

*Color of leaf veins*.—About 146A on upper surface, about 146B, yellow-green on lower surface.

Flowers:

*Flower sex*.—Hermaphrodite.

*Fragrance*.—Moderately fragrant.

*Date of bloom*.—Late May when grown in Chisago City, Minn.

*Date of full bloom*.—Early June when grown in Chisago City, Minn.

*Type*.—Fertile, based on use in controlled crosses.

*Amount of pollen*.—Abundant.

*Color of pollen*.—4B, yellow.

*Petals are ovoid in shape, cohering at summit and separating at base*.—2.5 mm long; 1 mm wide at fused end; reflexed after dehiscence. Flower petals are typically five in number, and open from the bottom to the top and remain entire after separation. Apex of petals is concave. Base is smooth and about 2.4 mm in circumference. Margins are smooth and convexly curved.

*Shape of cluster*.—Slightly conical.

*Average floral cluster length*.—10.6 inches (27 cm).

*Average floral cluster diameter*.—5.9 inches (15 cm).

The values presented below are means (with ranges in parentheses) from vines observed during the 2010 growing season.

*Number of flowers per cluster* 118 (92-147).

*Size of individual flower*.—5.2 mm long, 3.9 mm wide.

*Color of stamen*.—Anther: 162C, grayed yellow.

*Color of filament*.—155A, white.

*Number of stamen*.—5.0 (4-6).

*Number of pistil*.—1 per flower.

*Length of pistil*.—2.4 mm.

*Color on upper surface of petal*.—145A, yellow-green.

*Color on lower surface of petal.*—149D, light green.

*Sepals.*—Five in number, and generally very poorly developed.

*Color of sepal.*—144A, yellow-green (both surfaces).

*Color of pistil.*—144A, yellow-green.

*Cluster peduncles.*—Length 1.2 inches (3 cm) to 3.5 inches (9 cm), diameter 0.8 inches (2.0 cm) to 2.4 inches (6.0 cm).

*Cluster peduncle color.*—141A, light green.

*Texture of peduncles.*—Smooth, glabrous.

Fruit:

*Maturity.*—Ripe for commercial harvesting and wine approximately mid September near Chisago City in east central Minnesota.

*Solids.*—Sugar: medium brix (19.1% to 22.6%).

*Juice pH.*—(3.10-3.41).

*Percent titratable acidity.*—(0.80-1.09%).

The values presented below are means (with ranges in parentheses) from fruit observed in the 2010 growing season.

*Seeds.*—Seeds: 2-4 seeds per berry. Seed length: 0.55 mm (0.50-0.55) to 0.63 mm (0.54-0.65). Seed width: 0.33 mm (0.31-0.36) to 0.39 mm (0.35-0.46). Seed weight: 0.020 g. to 0.033 g. Seed Color: 165A, 177A.

*Clusters.*—Generally large-sized clusters weighing 0.4 pounds (about 182 grams) to 1 pound (about 454 grams). Clusters are loose and form a conical shouldered cluster.

*Size of cluster.*—13.2 cm long (10.3-16.7); 5.9 cm wide (3.7-7.2). Between 45 and 90 berries are included in a typical cluster.

*Clusters per plant.*—12.3.

*Clusters per shoot.*—1.8 clusters per shoot. Pedicel length ranges from 0.32 inches (8.0 mm) to 0.52 inches (13.0 mm). Pedicel diameter ranges from 0.06 inches (1.5 mm) to 0.1 inches (2.5 mm) at mid-pedicel. Pedicel texture — smooth, glaborous. Pedicel color — grayed-yellow 162A. The berry attachment is very strong. Almost no shatter occurs at full maturity.

*Berries.*—Berry size is medium and berry form is uniform. For example, the dimension of berries along the longitudinal axis is 0.4375 inch (about 11 mm) to 0.5 inch (12.7 mm). The dimensions of berries along the transverse axis is 0.5 inch (12.7 mm) to 0.75 inch (about 19 mm).

*Berry weight.*—0.07 ounces (about 2 grams) to 0.14 ounces (about 4 grams).

*Form.*—Round.

*Skin thickness.*—Medium.

*Texture.*—Firm.

*Tendency to split.*—None.

*Color.*—202A black with 98D bluish bloom. Color of flesh 63C light pink.

*Flavor.*—Sweet crisp.

*Eating quality.*—Good.

*Use.*—Wine (including late harvest wine and traditional Ice Wine), juice.

*Shipping and handling qualities.*—Excellent.

*Keeping quality.*—After two months in cold storage, still in good appearance.

Vineyard performance: Based on observations compiled over 4 years (2007-2010).

*Susceptibility to powdery mildew* (*Uncinula necator*).—Low.

*Susceptibility to downy mildew* (*Plasmopara viticola*) .—Moderate.

*Susceptibility to black rot* (*Guignardia bidwellii*).—Low.

*Susceptibility to foliar phylloxera* (*Daktulospahira vitifoliae)*.—Moderate.

*Susceptibility to crown gall* (*Agrobacterium*).—No natural infection observed.

*Susceptibility to phenoxy herbicide drift.*—Low.

*Winter hardiness.*—Trunks have survived −40.degree. F. (−40.degree. C.).

*Wood ripening.*—Good.

Wine quality: Descriptions below are compiled from observations on wine made from 'Nokomis' fruit harvested during the 2009-2010 growing seasons. 1. Flavors and aromas: black raspberry, cherry, blueberry, plum; no herbaceous aroma or very slight *V. labrusca* aroma. 2. Balance: medium body, well balanced when finished with residual sugar. 3. Color: attractive deep red color. 4. Propensity for oxidation: low. 5. Overall quality: excellent.

The invention claimed is:

1. A new and distinct variety of grapevine plant designated 'Nokomis' as illustrated and described herein.

* * * * *